(12) United States Patent
Lovell et al.

(10) Patent No.: US 9,498,255 B2
(45) Date of Patent: Nov. 22, 2016

(54) TRANSLATIONAL PEDICLE SCREW SYSTEMS

(71) Applicant: BLACKSTONE MEDICAL, INC., Lewisville, TX (US)

(72) Inventors: John Lovell, North Bergen, NJ (US); Tara Ziolo, Hewitt, NJ (US); Francesco Larosa, Neptune, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 26 days.

(21) Appl. No.: 14/145,003

(22) Filed: Dec. 31, 2013

(65) Prior Publication Data

US 2015/0182261 A1  Jul. 2, 2015

(51) Int. Cl.
*A61B 17/70* (2006.01)
(52) U.S. Cl.
CPC ........ *A61B 17/7037* (2013.01); *A61B 17/7035* (2013.01)
(58) Field of Classification Search
CPC ........................ A61B 17/7035; A61B 17/7037
USPC .................................................. 606/264–272
See application file for complete search history.

(56) References Cited

U.S. PATENT DOCUMENTS

| 7,955,358 | B2* | 6/2011 | Albert | A61B 17/7034 606/266 |
| 8,012,183 | B2* | 9/2011 | Alain | A61B 17/7038 606/264 |
| 8,323,290 | B2 | 12/2012 | Metzger et al. | |
| 8,394,133 | B2 | 3/2013 | Jackson | |
| 8,449,578 | B2* | 5/2013 | Keiser | A61B 17/7032 606/264 |
| 8,591,515 | B2* | 11/2013 | Jackson | A61B 17/7037 606/86 A |
| 2004/0138662 | A1* | 7/2004 | Landry | A61B 17/1604 606/86 A |
| 2007/0274800 | A1* | 11/2007 | Mikkonen | A61B 17/862 411/15 |
| 2008/0108992 | A1* | 5/2008 | Barry | A61B 17/7037 606/258 |
| 2010/0160975 | A1* | 6/2010 | Biedermann | A61B 17/7032 606/302 |
| 2012/0016425 | A1* | 1/2012 | Shaffrey | A61B 17/7032 606/305 |

(Continued)

*Primary Examiner* — Ellen C Hammond
*Assistant Examiner* — Stuart S Bray
(74) *Attorney, Agent, or Firm* — Baker & McKenzie LLP

(57) ABSTRACT

The present disclosure relates, according to some embodiments, to translational pedicle screw systems. A translational pedicle screw system may comprise a bone screw secured within a saddle. Different mechanisms may provide for translational movement of the saddle relative to the bone screw. In some embodiments, a saddle may comprise an elongated distal channel configured to provide a translational motion of a bone screw head disposed therein. In some embodiments, a saddle may comprise a discoidal recess configured to receive a corresponding discoidal section of a bone screw. The discoidal recess and the discoidal section may allow for a rotational offset of the saddle relative to the bone screw. In some embodiments, a proximal portion of a bone screw may comprise an attachment section configured to engage with a removable bone screw head. The removable bone screw head may translate laterally along the attachment section of the bone screw.

14 Claims, 9 Drawing Sheets

(56) References Cited

U.S. PATENT DOCUMENTS

| | | | |
|---|---|---|---|
| 2012/0277805 A1* | 11/2012 | Farris | A61B 17/7037 606/305 |
| 2013/0197586 A1* | 8/2013 | Matthis | A61B 17/7035 606/278 |
| 2014/0025119 A1* | 1/2014 | Biedermann | A61B 17/7032 606/266 |
| 2014/0046374 A1* | 2/2014 | Asaad | A61B 17/8605 606/267 |
| 2014/0081334 A1* | 3/2014 | Jackson | A61B 17/7035 606/278 |
| 2015/0100096 A1* | 4/2015 | Protopsaltis | A61B 17/7041 606/306 |
| 2015/0142059 A1* | 5/2015 | Biedermann | A61B 17/7035 606/266 |

* cited by examiner

TRANSLATIONAL PEDICLE SCREW SYSTEMS

FIELD OF THE DISCLOSURE

The present disclosure relates, in some embodiments, to pedicle screw systems. More specifically, embodiments of the present disclosure may provide for pedicle screw systems wherein a pedicle screw may have translational movement or translational freedom.

BACKGROUND OF THE DISCLOSURE

The spinal column of bones is a highly complex anatomical structure that includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction. The more than 20 discrete bones of an adult human spinal column are anatomically categorized as one of four classifications—cervical, thoracic, lumbar, or sacral—and are coupled together sequentially to one another by a tri-joint complex that consists of an anterior disc and two posterior facet joints. The anterior discs of adjacent bones are cushioned by cartilage spacers referred to as intervertebral discs or vertebrae. The cervical portion of the spine comprises the top of the spine up to the base of the skull and includes the first seven vertebrae. The intermediate 12 bones are thoracic vertebrae, and connect to the lower spine comprising the 5 lumbar vertebrae. The base of the spine comprises sacral bones, including the coccyx. With its complex nature, however, there is also an increased likelihood that surgery may be needed to correct one or more spinal pathologies.

Various systems exist for connecting fastener elements (e.g., pedicle screws) to bones for the purposes vertebral fixation. Such systems may use a plurality of bone screws fitted in saddles, wherein a plurality of saddles are aligned using a mounting rod. Alignment of mounting rods through positionally fixed saddles may be challenging. If a saddle is not in an appropriate position or an aligned position, the bone screw may have to be removed or repositioned, or the saddle may have to be refitted. In some situations, the mounting rod may have to be bent to align with the saddle at a fixed position. In some situations, additional components, such as offset connectors, may have be introduced to a bone screw system, such that a series of saddles may be aligned and secured by a mounting rod.

SUMMARY

Accordingly, a need has arisen for improved bone screw systems that may provide for saddles with translational movement or other degrees of movement.

The present disclosure relates, according to some embodiments, to spinal fixation systems that may comprise a bone screw, a saddle, a pressure cap, and a retaining ring. The bone screw may comprise a bone screw head at a proximal end and a shank portion at a distal end. The saddle may comprise a mounting rod receiving channel disposed at a proximal end of the saddle and a distal channel disposed at a distal end of the saddle. A distal channel may be configured to receive a retaining ring and the bone screw head therein. The pressure cap may be configured to be disposed within the saddle and between a mounting rod and the bone screw. A pressure cap may comprise a proximal portion configured to fit within an undercut of the saddle and a distal portion comprising an annular extension. The retaining ring may be configured to be disposed within the distal channel of the saddle. An outer circumference of the retaining ring may be adjacent to an inner wall of the distal channel of the saddle. The distal channel of the saddle may be configured to provide translational motion of the bone screw along a translational axis within the saddle.

The bone screw head comprise a recess thereon, wherein the recess may be operable to engage with a fastening mechanism. The shank portion may comprise threading thereon configured to be secured into a pedicle portion of a bone. The mounting rod receiving channel may be configured to receive a mounting rod therein. The proximal end of the mounting rod receiving channel may comprise an internal thread for receiving a compression element therein. The annular extension of the pressure cap may be configured to bias against the bone screw head of the bone screw. The saddle may further comprise at least one saddle pin hole disposed on a wall of the saddle. The pressure cap may further comprise at least one pressure cap pin hole disposed on a wall of the pressure cap; wherein the at least one saddle pin hole may be configured to align with at least one pressure cap pin hole; and wherein a holding pin may be received through the aligned saddle pin hole and pressure cap pin hole. The bone screw may have about 5 mm of translational motion about the translational axis. The translational axis may be substantially orthogonal to a longitudinal axis of the saddle passing from the proximal end to the distal end. The pressure cap and the retaining ring may comprise materials such as nitinol, titanium alloy, or cobalt chrome (CoCr). The saddle may have a length of about 5 mm to about 12. The saddle may have a width of about 5 mm to about 8 mm.

According to another aspect of the disclosure, methods of assembling a spinal fixation system may comprise providing a saddle; disposing a pressure cap within the saddle; disposing a retaining ring within the distal channel of the saddle such that an outer circumference of the retaining ring is adjacent to an inner wall of the proximal channel of the saddle; and receiving in the distal channel a bone screw head of a bone screw.

The present disclosure relates, according to some embodiments, to spinal fixation systems that may comprise a bone screw and a saddle. The bone screw may comprise a distal end comprising a shank portion and a proximal end comprising a discoidal section. A center of the discoidal section may be offset from a center axis of the shank portion. A saddle may comprise a mounting rod receiving channel disposed at a proximal end of the saddle and a discoidal recess disposed at a distal end of the saddle. The discoidal recess may be configured to receive the discoidal section of the bone screw. The discoidal section may have rotational freedom within the discoidal recess.

The shank portion may comprise threading thereon configured to be secured into a pedicle portion of a bone. The discoidal section and the shank portion may be monolithic in construction. The mounting rod receiving channel may be configured to receive a mounting rod therein. The proximal end of the mounting rod receiving channel may comprise an internal thread for receiving a compression element therein. A center of the discoidal recess may be offset from a longitudinal axis of the saddle passing from the proximal end to the distal end. The discoidal section may comprise an annular recess configured to receive a retention clip therein. The discoidal recess may comprise an annular recess configured to receive a retention clip when the saddle is attached to the bone screw. The discoidal section may have a diameter of about 4.5 mm to about 8 mm.

According to another aspect of the disclosure, methods of assembling a spinal fixation system may comprise providing a bone screw, wherein the bone screw may comprise a discoidal section at a proximal end. A center of the discoidal section may be offset from a center axis of the shank portion. Methods may further comprise disposing the discoidal section in a discoidal recess of a saddle, wherein the discoidal section may have a rotational freedom within the discoidal recess.

The present disclosure relates, according to some embodiments, to spinal fixation systems that may comprise a bone screw and a saddle. The bone screw may comprise a proximal end, wherein the proximal end may comprise an attachment section and wherein the attachment section may be configured to removably engage with a removable bone screw head. The bone screw may comprise a distal end, wherein the distal end comprises a shank portion. The saddle may comprise a mounting rod receiving channel disposed at a proximal end of the saddle and a distal recess disposed at a distal end of the saddle. The distal recess may be operable to receive the removable bone screw head therein.

Removably engaging the attachment section with the removable bone screw head may comprise securing a lateral pin of the removable bone screw head in a lateral recess of the attachment section. The lateral pin may be operable to translate within the lateral recess when secured therein. The range of translational movement may be about 5 mm.

The removable bone screw head may comprise a recess thereon, the recess operable to engage with a fastening mechanism. The shank portion may comprise threading thereon configured to be secured into a pedicle portion of a bone. The mounting rod receiving channel may be configured to receive a mounting rod therein. The proximal end of the mounting rod receiving channel may comprise an internal thread for receiving a compression element therein. The distal recess may further comprise a proximal undercut configured to receive at least one biasing component. The at least one biasing component may be a wave spring. The saddle may have a height of about 3 mm to about 8 mm. Compression of opposing sides of the proximal end of the saddle may be operable to expand the distal recess of the saddle. The spinal fixation system may further comprise a pressure cap operable to be disposed distal to the proximal end of the saddle and to bias against the removable bone screw head. The pressure cap may be monolithic with the saddle.

According to another aspect of the disclosure, methods of assembling a spinal fixation system may comprise providing a bone screw, wherein a proximal end of the bone screw may comprise an attachment section. Methods may further comprise removably engaging the attachment section with a removable bone screw head, and receiving the removable bone screw head in a distal recess of a saddle.

BRIEF DESCRIPTION OF THE DRAWINGS

Some embodiments of the disclosure may be understood by referring, in part, to the present disclosure and the accompanying drawings, wherein.

DETAILED DESCRIPTION

The present disclosure relates, in some embodiments, to pedicle screw systems. More specifically, embodiments of the present disclosure may provide for pedicle screw systems wherein a pedicle screw may have translational movement or translational freedom. Pedicle screw systems of the present disclosure may comprise a bone screw and a saddle, wherein the bone screw may be disposed within the saddle. The bone screw may be secured or fastened into a pedicle region of the spine. Such securing or fastening may occur before or after the bone screw is disposed within the saddle. Embodiments of the present disclosure may advantageously provide for bone screws that may have translational movement or translational freedom within a saddle. Such embodiments may advantageously allow a position of the saddle relative to the bone screw to be adjusted such that a mounting rod may be more easily aligned between multiple saddles.

The present disclosure provides for various embodiments of translational pedicle screws. Provided below are descriptions for three embodiments of the present disclosure. Such embodiments and description thereof is provided by way of example only and is not intended to limit the scope of the present disclosure. One of ordinary skill in the art would appreciate that various changes in the shape, size, number, and/or arrangement of parts may be made without departing from the present disclosure. Various features and designs of the example embodiments may be altered or combined to provide for pedicle screw systems encompassed by the present disclosure.

Embodiment A

Figure 1:
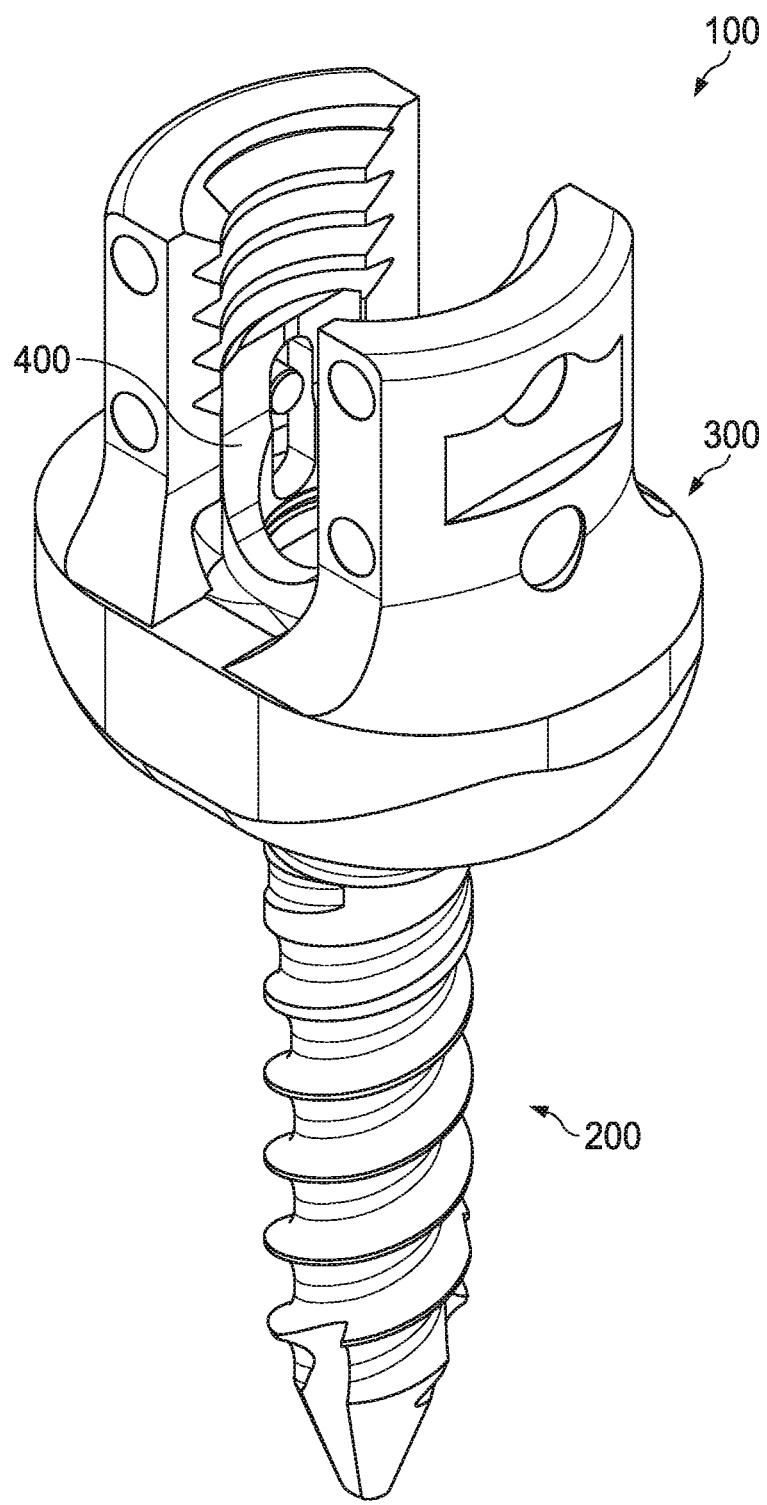
FIG. 1 illustrates a perspective view of a translational pedicle screw system according to one embodiment of the present disclosure.

Referring to FIG. 1, a perspective view of a translational pedicle screw system 100 according to one embodiment of the present disclosure is shown. As shown in FIG. 1, the pedicle screw system 100 may comprise a bone screw 200, a saddle 300, and a pressure cap 400. The bone screw 200 may be disposed within the saddle 300. The pressure cap 400 may be disposed within the saddle 300 above the bone screw 200.

Figure 2:
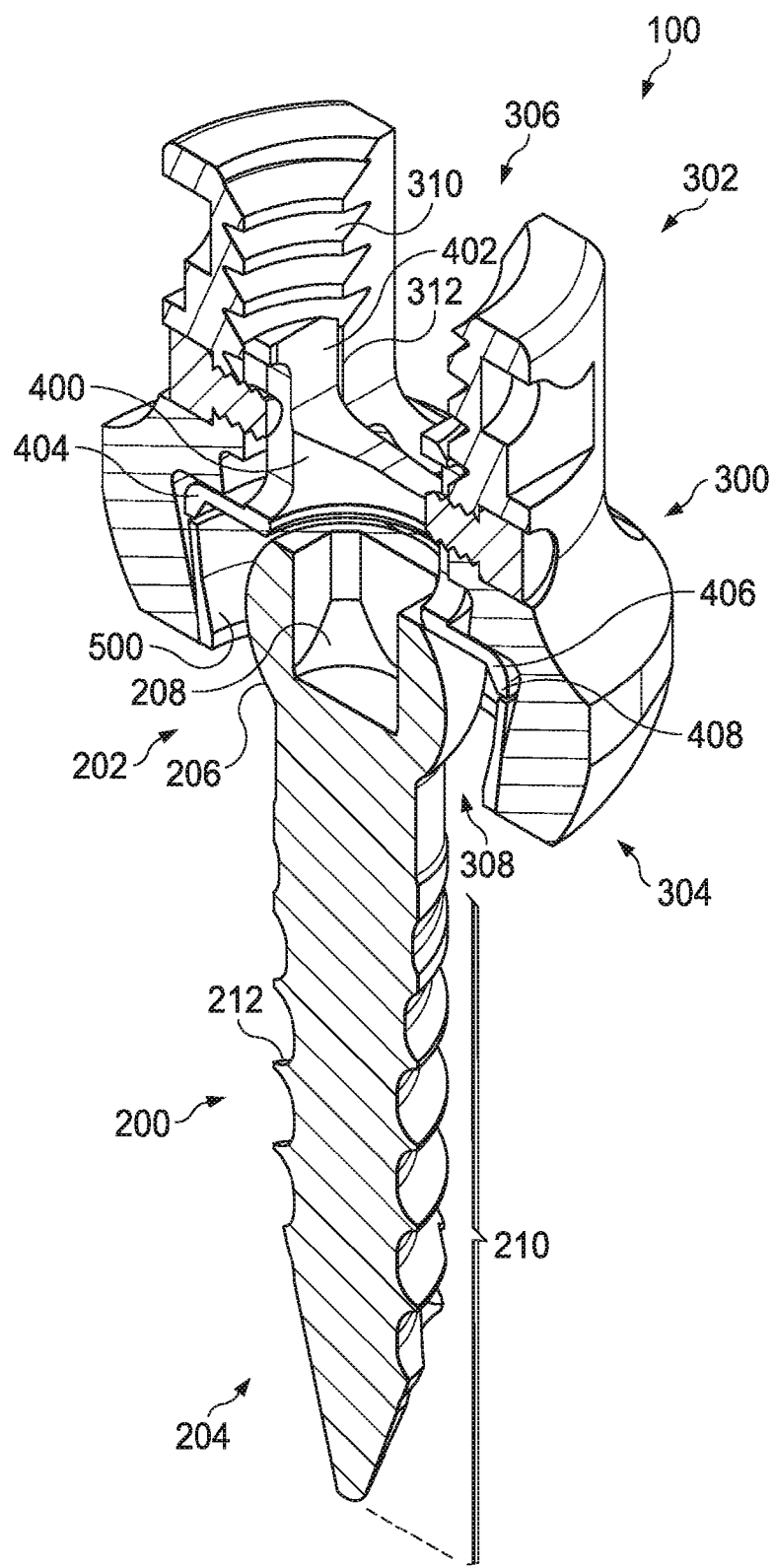
FIG. 2 illustrates a cross-sectional perspective view of a translational pedicle screw system according to the embodiment shown in FIG. 1.

Referring to FIG. 2, a cross-sectional perspective view of the translational pedicle screw system 100 of FIG. 1 is shown. As shown in FIG. 2, the bone screw 200 may comprise a bone screw head 206 at a proximal end 202 of the bone screw 200. The bone screw head 206 may comprise a spherical geometry, wherein the spherical geometry may advantageously promote a rotation of the bone screw 200 within the saddle 300. Such rotation may advantageously provide for a multi-axial bone screw system 100. The bone screw head 206 may comprise a recess 208 thereon. The recess 208 may comprise a particular geometry operable to receive or engage with a corresponding feature therein. For example, the recess 208 may comprise a rectangular, hexagonal, octagonal, hex, or star shape geometry. Such recess 208 may be operable to receive a corresponding feature on a fastening mechanism or device such as a screw driver or counter-torque wrench. A fastening mechanism may be used to rotate, fasten, or otherwise secure the bone screw 200 into a pedicle portion of a spine. Such rotation or fastening may be performed before, during, or after the saddle 300 or other components of the pedicle screw system 100 have been assembled.

A bone screw 200 may comprise a shank portion 210 at a distal end 204 of the bone screw 200. The shank portion 210 may comprise a threading 212 thereon. The threading 212 may be configured or designed to promote the fastening of the bone screw 200 into a pedicle portion of a spine. One of ordinary skill in the art would appreciate that variations may be made to the angle, pitch, thickness, and other dimensions of the threading 212 without departing from the present disclosure.

The saddle 300 may comprise a mounting rod receiving channel 306 disposed at a proximal end 302 of the saddle 300, and a distal channel 308 disposed at a distal end 304 of the saddle 300. The mounting rod receiving channel 306 at the proximal end 302 of the saddle 300 may be operable to receive a mounting rod therein. A mounting rod may be received in an orientation substantially orthogonal to a longitudinal axis of the saddle 300. A longitudinal axis may be defined as an axis passing from the proximal end 302 to the distal end 304 of the saddle 300. A distal portion of the mounting rod receiving channel 306 may comprise a curved surface, wherein the curved surface may be configured or designed to contour against a portion of a circumferential surface of a mounting rod.

In some embodiments, the proximal end 302 of the mounting rod receiving channel 306 may comprise an internal threading 310 operable to receive a compression element therein. The internal threading 310 may be exposed even when a mounting rod has been received and disposed within the mounting rod receiving channel 306. Various aspects of the internal threading 310 such as a pitch, angle, and/or thickness of threads may be adjusted to achieve various design or functional goals. For example, various pitches and angles may allow the internal threading 310 to mate with a compression element with a compressing thread. A compression element may be a set screw or other fastener. A set screw may bias against a mounting rod disposed within the mounting rod receiving channel 306 and thereby exert pressure or compressive forces on components distal to the set screw. Components distal to the set screw may include a mounting rod, the pressure cap 400, a retaining ring 500, and/or the bone screw 200.

The distal channel 308 at the distal end 304 of the saddle 300 may be configured to receive the retaining ring 500 and the bone screw head 206. Described further, both the retaining ring 500 and the bone screw head 206 may rest within the distal channel 308. In some embodiments, the distal channel 308 may comprise a rectangular geometry. In some embodiments, the distal channel 308 may comprise an elongated geometry which may allow the bone screw head 206 to translate along an axis or direction of the distal channel 308. Variations may be made to the size and dimensions of the distal channel 308 without departing from the present disclosure.

In some embodiments, the retaining ring 500 may be disposed within the distal channel 308. The retaining ring 500 may be configured to be disposed within the distal channel 308 such that an outer circumference of the retaining ring 500 may be adjacent to an inner wall of the distal channel 308. Described differently, the retaining ring 500 may contour against the inner walls or inner circumference of the distal channel 308. The retaining ring 500 may be disposed within the distal channel 308 by first compressing the retaining ring 500 and then allowing it to expand against the walls of the distal channel 308. Such expansion may advantageously allow the retaining ring 500 to be secured within the distal channel 308. Further, such expansion may advantageously provide an expansive force against the distal channel 308 of the saddle 300 and thereby create additional compressive or frictional forces within the saddle 300. Such forces may advantageously allow for a more secure and stable pedicle bone screw system 100.

In some embodiments, the pressure cap 400 may be disposed within the saddle 300. The pressure cap 400 may be positioned above the bone screw head 206 of the bone screw 200 and below the internal threading 310 of the proximal end 302 of the saddle 300. The pressure cap 400 may be disposed between a mounting rod and the bone screw 200 such that securing a mounting rod into the saddle may apply a compressive force on the pressure cap 400 and on the bone screw 200. In some embodiments the saddle 300 may comprise an undercut 312. The undercut 312 may be a square pocket cut-out or some other geometric recess configured to receive a corresponding pressure cap 400. Thus, a proximal portion 402 of the pressure cap 400 may be configured to fit within the undercut 312 of the saddle 300.

The pressure cap 400 may further comprise an annular extension 406 at a distal portion 404. When the pressure cap 400 may be secured within the saddle 300, the annular extension 406 may be disposed within the distal channel 308 of the saddle 300. The annular extension 406 may be configured to contour against a portion of the bone screw head 206 and bias against the bone screw head 206. In some embodiments, the annular extension 406 may further comprise a protruding edge 408. The protruding edge 408 may be oriented downwards or distally, and may be configured to rest on a top surface of the retaining ring 500 and thereby bias against or exert a compressive force thereon when the bone screw system 100 is assembled.

Figure 3:
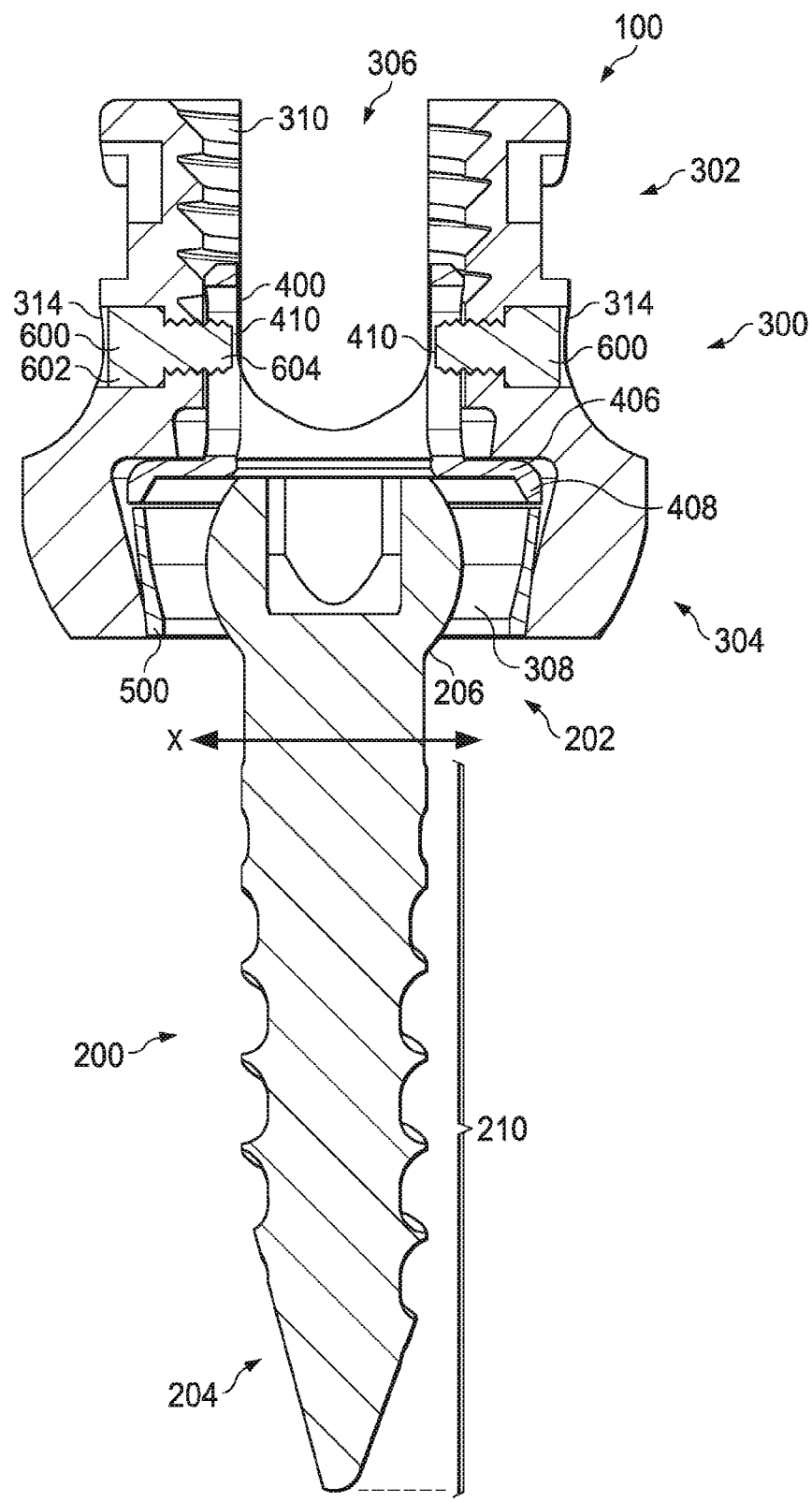
FIG. 3 illustrates a cross-sectional profile view of a translational pedicle screw system according to the embodiment shown in FIG. 1 and FIG. 2.

Referring to FIG. 3, a cross-sectional profile view of the translational pedicle screw system 100 of FIG. 1 and FIG. 2 is shown. As shown in FIG. 3, the saddle 300 of the bone screw system 100 may further comprise at least one saddle pin hole 314 disposed on a wall of the saddle 300. In some embodiments, the saddle 300 may comprise two saddle pin holes 314 dispose across from one another on opposing walls of the saddle 300. Similarly, the pressure cap 400 may comprise at least one pressure cap pin hole 410 disposed on a wall of the pressure cap 400. In some embodiments, the pressure cap 400 may comprise two pressure cap in holes 410 disposed across from one another on opposing walls of the pressure cap 400. As shown in FIG. 3, the saddle pin hole 314 may be configured to align with the pressure cap pin hole 410. Alignment of the saddle pin hole 314 and the pressure cap pin hole 410 may allow a holding pin 600 to be received therethrough. As shown in FIG. 3, one holding pin 410 may be disposed within each of the two aligned pressured cap pin holes 410 and saddle pin holes 314.

The dimensions of the holding pin 600 may be varied without departing from the present disclosures. The holding pin 600 may have a larger or smaller diameter or other measurements as needed or desired to accomplish various functional purposes. For example, a larger holding pin 600 may be more easily manipulated or handled during surgery. A larger holding pin 600 may be more sturdy and may better secure the pressure cap 400 to the saddle 300. A smaller holding pin 600 may advantageously be used in smaller, less-invasive bone screw systems 100. Smaller holdings pin 600 would require smaller corresponding pressured cap pin holes 410 and saddle pin holes 314. Thus, the dimensions of the bone screw system 100 may advantageously be more compact as well.

The holding pin 600 may also comprise multiple sections. For example, the holding pins 600 shown in FIG. 3 may comprise a larger stopper section 602 with a greater radius and a smaller fastening section 604 with a smaller radius. The stopper section 602 may have a greater radius and such greater radius may allow this section to be more easily manipulated or handled during surgery. The fastening section 604 may have a smaller radius which may advantageously allow for greater ease in fastening or otherwise inserting the holding pin 600 through the aligned pressure cap pin holes 410 and saddle pin holes 314.

Embodiments of the present disclosure may advantageously provide for translational pedicle screws. For example, the bone screw 200 may have a translational motion or translation freedom of movement along a translational axis within the distal channel 308 of the saddle 300. The translational axis may be substantially orthogonal to a longitudinal axis of the saddle 300 passing from the proximal end 302 to the distal end 304. In FIG. 3, the translational axis is indicated as the X axis. Described further, the distal channel 308 may comprise an elongated geometry having a longer length in one direction and a shorter length in an orthogonal direction. The shorter length may be sufficient to receive and to secure the bone screw head 206 along the direction of the shorter length within the distal channel 308. The longer length, or the length along the X axis in FIG. 3, may allow the bone screw head 206 to translate along said length or axis within the distal channel 308.

A range of translational motion may vary without departing from the present disclosure. The range of translational motion available to the bone screw head 206 may depend on the dimensions of the bone screw head 206 and the dimensions of the distal channel 308. In some embodiments, the bone screw 200 may have about 5 mm of translational movement along axis X. The range of translational movement may be increased or decreased by adjusting dimensions of the saddle 300 and/or dimensions of the distal channel 308 corresponding to axis X. Elongating the saddle 300 and the distal channel 308 may advantageously provide for a greater range of translational motion. However, elongating the saddle 300 and the distal channel may require a larger saddle 300 and, as a result, larger incision to be made during surgery. Shortening the length of the saddle 300 and the distal channel 308 along the X axis may advantageously provide for a more compact system, but may reduce the range of translational motion provided to the bone screw 200.

Embodiments of the present disclosure may advantageously provide for a translational motion of the bones crew along the X axis. The bone screw 200 may also have additional degrees of movement such as a rotational movement about the longitudinal axis of the bone screw 200. For example, the bone screw 200 having a substantially spherical bone screw head 206 may be able to rotate or pivot, even if the bone screw head 206 remains stationary in its position in the distal channel 308 along the X axis. Such ranges of motion may allow the bone screw 200 to be secured into a pedicle region of a spine with greater ease, and may allow the saddle 300 to have positional freedom relative to the bone screw 200 such that a mounting rod may be aligned through the saddle 300 with greater ease.

In any of the embodiments of the present disclosure, the materials may be chosen and may be varied to fit a number of functional and design considerations. For example, the bone screw 200, the saddle 300, and the holding pins 600 may comprise materials such as titanium, titanium alloys (ex. Ti-6Al-4V), aluminum, stainless steel, or cobalt chrome alloy, polymer (ex. Radel, Ultem, or PEEK) or carbon filled polymer. Components such as the pressure cap 400 and the retaining ring 500 may comprise similar materials.

In some embodiments, the pressure cap and the retaining ring 500 may comprise nitinol. Nitinol may have elastic qualities such as superelasticity or pseudoelasticity that may allow the material to be more resistant to stress, strain, and/or other deformations. Such properties may provide for various advantages in pedicle screw systems 100. For example, the retaining ring 500 comprising nitinol may be more readily deformed or compressed. In a deformed or compressed state, the retaining ring 500 may be more easily received into the distal channel 308. For example, a user (i.e., a surgeon) may squeeze the retaining ring 500 to compress a length of the retaining ring. Then, the retaining ring 500 may be positioned into the distal channel 308. Once received into the distal channel 308, the retaining ring 500 may be released thereby allowing the retaining ring 500 to expand to its original dimensions, free of deformations. Thus, use of nitinol as materials for components such as the retaining ring 500 may advantageously provide for greater ease in assembly of the bone screw system 100.

Embodiments of the present disclosure may comprise components with various dimensions and measurements. In some embodiments, the saddle 300 may have a height of about 3 mm to about 8 mm. The saddle 300 may have a width of about 5 mm to about 12 mm. The saddle 300 may have a length of about 5 mm to about 8 mm. The length of the saddle 300 may influence the range of translation motion that the bone screw head 206 may have in the saddle 300. In some embodiments, the retaining ring 500 may have a shorter dimension of about 8 mm to about 10 mm. A shorter dimension of the retaining ring 500 may correspond to a diameter or the bone screw head 206. Further, the retaining ring may have a longer dimension of about 8 mm to about 15 mm. The longer dimension may correspond to a range of translation motion that the bone screw head 206 may have in the saddle 300. Dimensions of the various components of the present disclosure may be varied as needed or desired to achieve a number of functional or design goals. Such variations in dimensions may provide for translational pedicle screw systems 100 without departing from the present disclosure.

According to another aspect of the present disclosure, methods of assembling the translational pedicle screw system 100 are provided. Methods may comprise providing the saddle 300 and disposing, securing, or otherwise receiving the pressure cap 400 into the saddle 300. More specifically, the proximal portion 402 of the pressure cap 400 may be received into the undercut 312 of the saddle 300.

Methods may also comprise disposing, securing, or otherwise receiving the retaining ring 500 into the distal channel 308 of the saddle 300. The retaining ring 500 may be disposed by compressing the retaining ring 500 such that it may become slightly deformed. Then, the retaining ring 500 may be positioned within the distal channel 308 and released. A release of the retaining ring 500 may allow the retaining ring 500 to return to its original, undeformed shape or structure. In its original, undeformed shape or structure, the retaining ring 500 may contour against the inner wall of the distal channel 308 or be secured adjacent to the inner wall of the distal channel 308.

Methods may further comprise securing or otherwise receiving the bone screw head 206 into the distal channel 308 of the saddle 300. The bone screw head 206 may be disposed such that the annular protrusion 406 may bias against the bone screw head 206. The bone screw 200 may be secured to the saddle 300 either before or after the shank portion 210 of the bone screw 200 has been secured into a pedicle portion of the spine. The bone screw 200 may be fastened by engaging the recess 208 with a fastening device such as a set screw or a counter-torque wrench.

The bone screw 200 secured to the saddle 300 may have a translational freedom along an axis of the saddle 300. Thus, the saddle 300 may be allowed to slide or translate along the axis when the bones crew 200 is secured or fastened. Such translational movement may advantageously allow a position of the saddle 300 to be adjusted, which may allow for greater ease in aligning and receiving a mounting rod into the mounting rod receiving channel 306.

After a mounting rod is received into the mounting rod receiving channel 306, a compression element such as a set screw may be disposed and/or fastened into the inner threading 310 of the saddle 300. Fastening a set screw into the proximal portion 302 of the saddle 300 may exert a compressive force on the mounting rod which may provide increased pressure and frictional forces within the bone screw system 100. Such increased pressure and frictional forces may prevent the bone screw 200 and the saddle 300 from translating along the translational axis once the screw system 100 is fully assembled and secured.

Embodiment B

Figure 4:
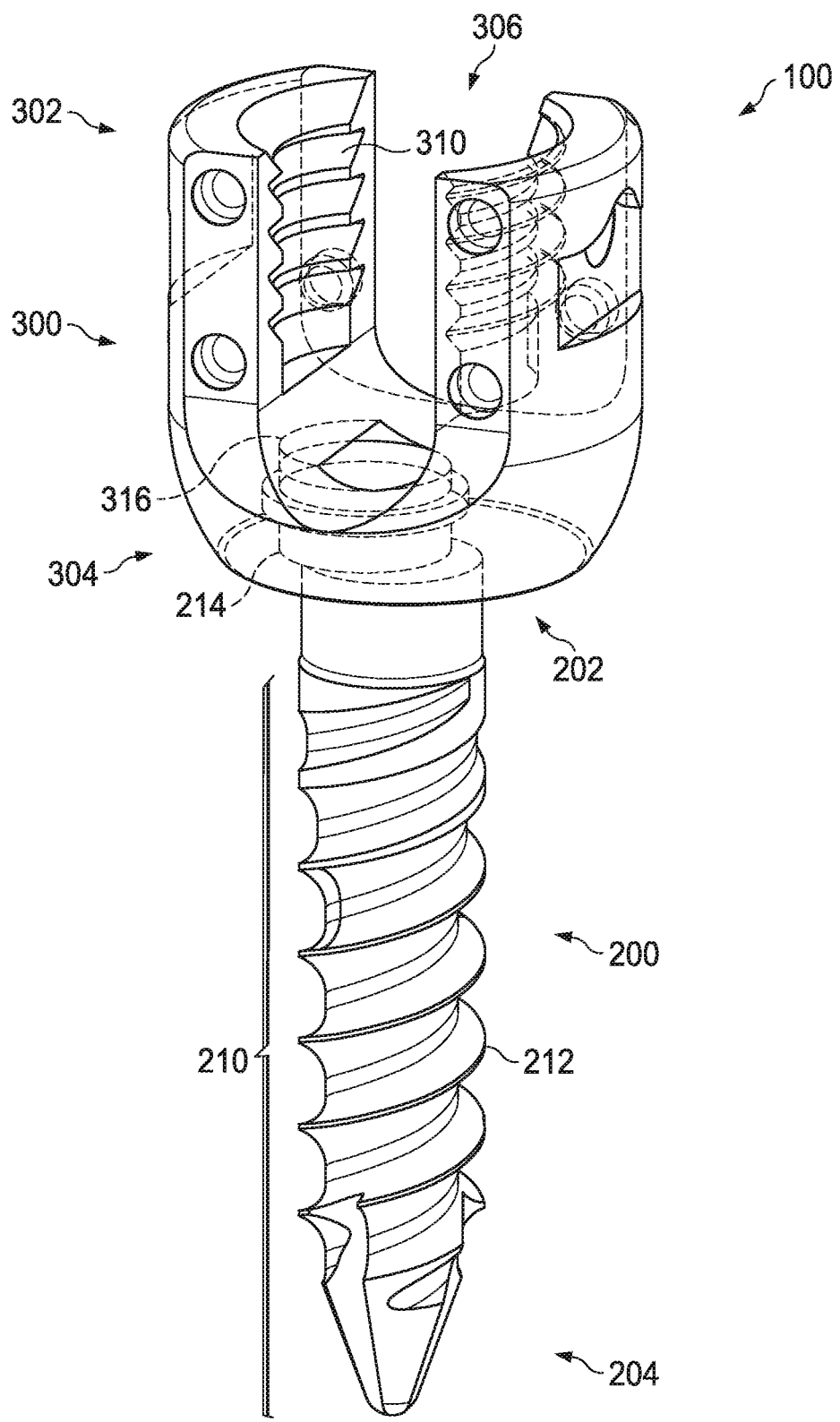
FIG. 4 illustrates a perspective view of a translational pedicle screw system according to one embodiment of the present disclosure.

Referring to FIG. 4, a perspective view of a translational pedicle screw system 100 according to another embodiment of the present disclosure is shown. The example embodiment shown in FIG. 4 may also comprise the bone screw 200 and the saddle 300.

As shown in FIG. 4, the bone screw 200 may comprise the distal end 204 comprising the shank portion 210. The shank portion 210 may comprise the threading 212 configured to allow the bone screw 200 to be fastened or otherwise secured into a bone. At the proximal end 202, the bone screw 200 may comprise a discoidal section 214. The discoidal section 214 may be flat, circular, and/or disc-like in shape and construction. In some embodiments, a center of the discoidal section 214 may be offset from a center axis of the shank portion 210. One of ordinary skill in the art would appreciate that the center axis of the shank portion 210 may pass from the proximal end 202 to the distal end 204 of the bone screw 200. Embodiments providing for the discoidal section 214 may allow the saddle 300 to rotate about the center of the discoidal section 214. Such rotation may allow the saddle 300 to be translated or otherwise positioned away from the center axis of the shank portion 210 of the bone screw 200. The degree or amount of offset of the discoidal section 214 from the shank portion 210 may vary as needed or desired to achieve various functional or design goals. For example, a larger offset may allow the saddle 300 to rotate further away relative to the center axis of the shank portion 210. However, the greater offset may result in more instability or risks of structural failure. In some embodiments, a smaller offset may advantageously provide for more stability and greater ease in manipulation during surgery and greater ease in manufacturing. However, a smaller offset may allow for a smaller displacement or translation of the saddle 300 away from the center axis of the shank portion 210.

In some embodiments, the discoidal section 214 and the shank portion 210 of the bone screw 210 may be monolithic in construction. Explained differently, the discoidal section 14 and the shank portion 210 may comprise the same material throughout and may be machined or otherwise manufactured from a single piece of material. One of ordinary skill in the art would appreciate that various methods may be used to machine or fashion particular shapes or geometries into a single piece of material. Such methods may be used to provide the discoidal section 214 having an offset from the shank portion 210 of the bone screw 200. Variations in such methods may be used without departing from the scope of the present disclosure.

In some embodiments, a top of the discoidal section 214 may be exposed when secured within the saddle 300. The top of the discoidal section 214 may comprise a geometric recess such as a square, hex, star, or other polygon. Thus, when exposed through the discoidal recess 316 of the saddle 300, such geometric recess may be operable to receive a corresponding geometric feature on, for example, a fastening device. A fastening device may be a screw driver or counter torque wrench. Use of a fastening device may allow or promote fastening or securing of the bone screw 200 into the bone.

As shown in FIG. 4, the saddle 300 may comprise the mounting rod receiving channel 306 disposed at the proximal end 302 of the saddle 300. The saddle 300 may further comprise a discoidal recess 316 at the distal end 304 of the saddle 300. The discoidal recess 316 may be a flat, circular, and/or disc-like recess at the base or the distal end 304 of the saddle. In some embodiments, the discoidal recess 316 may have dimensions corresponding to the discoidal section 214 of the bone screw 200. Corresponding dimensions may advantageously allow the discoidal recess 316 to receive the discoidal section 214 of the bone screw 200. Described differently, the discoidal section 214 may be configured to be fitted within or otherwise disposed within the discoidal recess 316. Once disposed therein, a circular or disc-like construction of the discoidal section 214 and a corresponding circular or disc-like geometry of the discoidal recess 316 may allow the discoidal section 214 to have a rotational freedom within the discoidal recess 316.

The saddle 300 may further comprise the mounting rod receiving channel 306 at the proximal end 302. The mounting rod receiving channel 306 may be configured to receive a mounting rod therein. A received mounting rod may bias against components within the saddle 300 and thereby promote greater security and stability within the bone screw system 100. The mounting rod and other components disposed within the saddle 300 may be positionally secured by a compression element such as a set screw. The proximal end 302 of the saddle 300 may comprise internal threading 310 configured to receive a compression element such as a set screw therein.

Figure 5B:
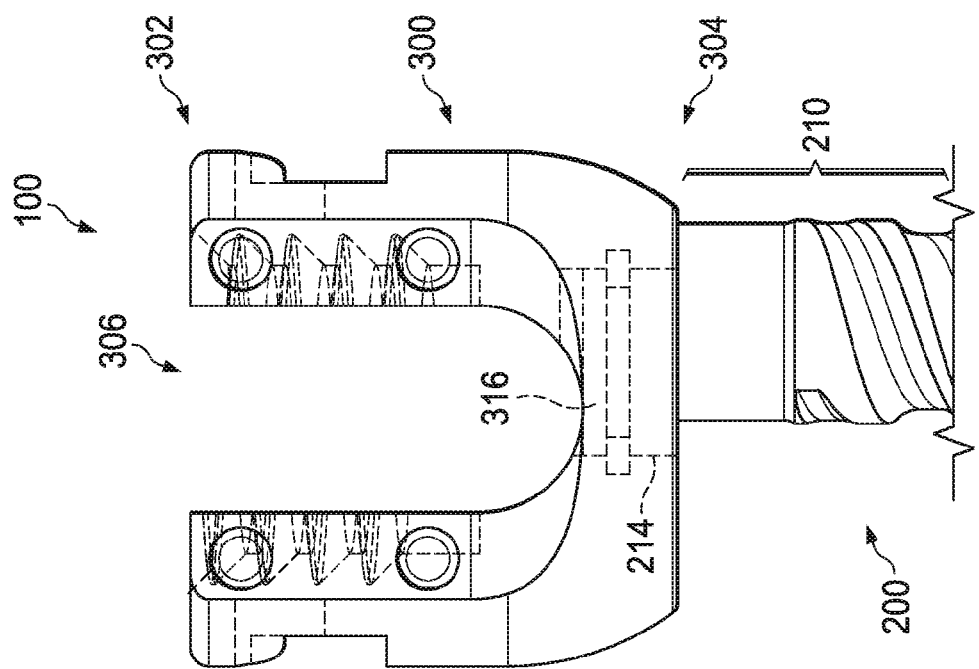
FIG. 5B illustrates a close-up, cross-sectional profile view of a translational pedicle screw system according to the embodiment shown in FIG. 4 and FIG. 5A.
Figure 5A:
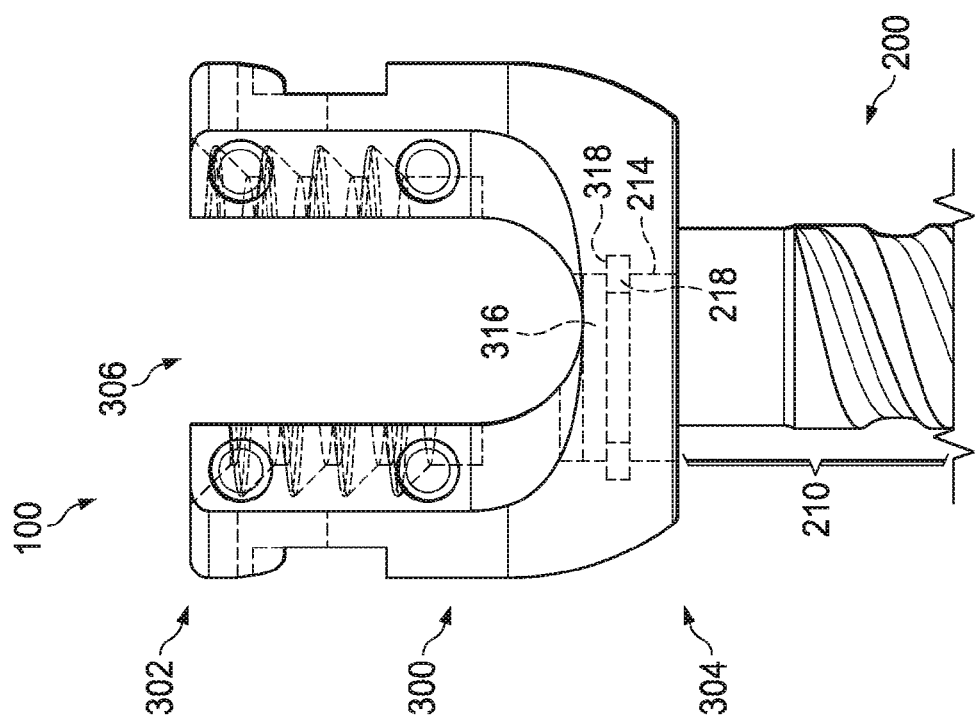
FIG. 5A illustrates a close-up, cross-sectional profile view of a translational pedicle screw system according to the embodiment shown in FIG. 4.

Embodiments of the present disclosure as shown in FIG. 4 may allow the saddle 300 to rotate about the discoidal section 214 of the bone screw 200. Such rotation may advantageously allow the saddle 300 to be positionally translated or displaced from a center axis of the bone screw 200. Different amounts or degrees of translation or displacement may be achieved by varying a placement of the discoidal recess 316 at the distal end 304 of the saddle 300. In some embodiments, the discoidal recess 316 may be offset from a longitudinal axis of the saddle 300 passing from the proximal end 302 to the distal end 304. Described differently, the discoidal recess 316 may not be positioned at a center of the base of the saddle 300 and may be offset from the center of the base of the saddle 300. For example, FIG. 5A illustrates a close-up, cross-sectional profile view of a translational pedicle screw system 100 according to the embodiment shown in FIG. 4. As shown in FIG. 5A, the discoidal recess 316 may not be centered about a longitudinal axis of the saddle 300. From the perspective shown in FIG. 5A, the discoidal recess 316 is offset to the left of the longitudinal axis of the saddle 300. FIG. 5A may depict an unrotated or untranslated orientation or position of the saddle 300 relative to the bone screw 200. As shown in FIG. 5A, a longitudinal axis of the saddle 300 may align with a longitudinal axis of the bone screw 200. The positioning of the saddle 300 relative to the bone screw 200 shown in FIG. 5A may be comparable to that of traditional bone screw systems. However, as shown in FIG. 5B, the saddle 300 of the present disclosure may translate or be displaced from its original position. FIG. 5B illustrates a close-up, cross-sectional profile view of a translational pedicle screw system 100 according to the embodiment shown in FIG. 4 and FIG. 5A. As shown in FIG. 5B, the saddle 300 may be rotated such that a longitudinal axis of the saddle 300 may not align with a longitudinal axis of the bone screw 200. Such displacement or translation of the saddle 300 may advantageously provide for greater freedom of movement of the saddle 300.

Additional components not shown in FIG. 4 may be disposed within the saddle 300 and may be part of the bone screw system 100. For example, the bone screw system 100 of FIG. 4 may further comprise a pressure cap which may be disposed within the saddle and may be operable to bias against a top of the discoidal section 214 or the discoidal recess 316. In some embodiments, the bone screw system 100 may further comprise pin holes along the saddle 300 configured to receive a pin or pins therein. Such pins may advantageously promote additional stability and security in the bone screw system 100.

Bone screw systems 100 may also comprise a keyed feature to temporarily secure the discoidal section 214 and the discoidal recess 316 in a centered position until such time that a user (e.g. a surgeon) may want to rotate the saddle 300 about the bone screw 200. A keyed feature may be a feature such as a square or oblong pin that may connect the discoidal section 214 to the shank portion 210. A keyed feature may advantageously prevent relative rotation until such time that a user (i.e. a surgeon) may desire such rotation or may disconnect the keyed feature.

In some embodiments, the discoidal section 214 of the bone screw 200 may comprise an annular recess 218 configured to receive a retention clip therein. The annular recess 218 may comprise an inward indentation along a circumference of the discoidal section 214. Such recess 218 or indentation may be positioned approximately at the middle of a height of a discoidal section 214. The circumferential or annular recess 218 may be configured to allow a retention ring or retention clip, which may have a circular geometry, to be received therein. The retention ring or retention clip may be squeezed to compress or deform a dimension of the ring or clip. Thus, the ring or clip may fit within the annual recess 218 of the discoidal section 214.

The bone screw system 100 may further comprise an annular recess 318 in the saddle 300. The annular recess 318 of the saddle may comprise an inward indentation along a circumferential surface of the discoidal recess 316. In some embodiments, when the discoidal section 214 is received within the discoidal recess 316, the annual recess 218 of the bone screw 200 may align with the annular recess 318 of the saddle 300. Thus, the annular recess 318 of the saddle 300 may be configured to receive a retention ring or retention clip from the annual recess 218 of the bone screw 200. Described differently, a retention ring or retention clip may first be compressed to fit within the annular recess 218 of the bone screw 200. Then, when the discoidal section 214 of the bone screw 200 is disposed within the discoidal recess 316 of the saddle 300, the retention ring or retention clip may expand from the annual recess 218 of the bone screw 200 into the annular recess 318 of the saddle. Such expansion or disposing of a retention ring or retention clip within the annular recess 318 of the saddle may advantageously allow a bone screw 200 to be locked or secured relative to the saddle 300. Once a retention ring or retention clip has expanded into the annular recess 318 of the saddle 300, there may no longer be any compressive forces available to compress the retention ring or retention clip. Thus, the bone screw 200 may be locked to the saddle 300.

In any of the embodiments of the present disclosure, the materials may be chosen and may be varied to fit a number of functional and design considerations. For example, the bone screw 200 and the saddle 300 may comprise materials such as titanium, titanium alloys (ex. Ti-6Al-4V), aluminum, stainless steel, or cobalt chrome alloy, nitinol, polymer (ex. Radel, Ultem, or PEEK) or carbon filled polymer. Embodiments of the present disclosure with a discoidal section 213 offset from a longitudinal axis of the bone screw 200 may benefit from being machined from sturdier materials. Components such as the retaining ring or clip may comprise similar materials or may comprise materials such as nitinol. Variations may be made to the composition of aforementioned components without departing from the present disclosure.

Embodiments of the present disclosure may comprise components with various dimensions and measurements. In some embodiments, the discoidal section 214 of the bone screw may have a diameter of about of about 4 mm to about 8 mm. The discoidal recess 316 of the saddle 300 may have corresponding dimensions such that the discoidal section 214 may be received therein. In some embodiments a center of the discoidal section 214 may be offset from the center axis of the bone screw 200 by about 3 mm to about 6 mm. One of ordinary skill in the art would appreciate that variations may be made to the dimensions of the components without departing from the present disclosure.

According to another aspect of the present disclosure, methods of assembling the translational pedicle screw system 100 are provided. Methods may comprise providing the saddle 300 and disposing, securing, or otherwise receiving the discoidal section 214 of the bone screw 200 into the discoidal recess 316 of the saddle 300. In some embodiments, methods may further comprise compressing a retention ring or retention clip within the annular recess 218 of the discoidal section 214. When the discoidal section 214 is received within the discoidal recess 316, the retention ring or retention clip may expand and/or lock into the annular recess 318 of the discoidal recess 316.

Methods may further comprise fastening the bone screw 200 into a pedicle portion of a spine. The bone screw 200 may be fastened into a pedicle portion of a spine either before or after the bone screw 200 has been secured to the saddle 300.

Methods may further comprise rotating the saddle 300 about the bone screw 200. The saddle 300 may be rotate about the bone screw 200 via a rotational movement provided by the disposing of the discoidal section 214 in the discoidal recess 316. Methods of the present disclosure may comprise rotating the saddle 300 such that the mounting rod receiving channel 306 is in a desired position or a convenient position to promote alignment of a mounting rod between a plurality of saddles 300 in a bone screw system 100.

After a mounting rod is received into the mounting rod receiving channel 306, a compression element such as a set screw may be disposed and/or fastened into the inner threading 310 of the saddle 300. Fastening a set screw into the proximal portion 302 of the saddle 300 may exert a compressive force on the mounting rod which may provide increased pressure and frictional forces within the bone screw system 100. Such increased pressure and frictional forces may prevent the bone screw 200 and the saddle 300 from translating along the translational axis once the screw system 100 is fully assembled and secured.

Embodiment C

Figure 6:
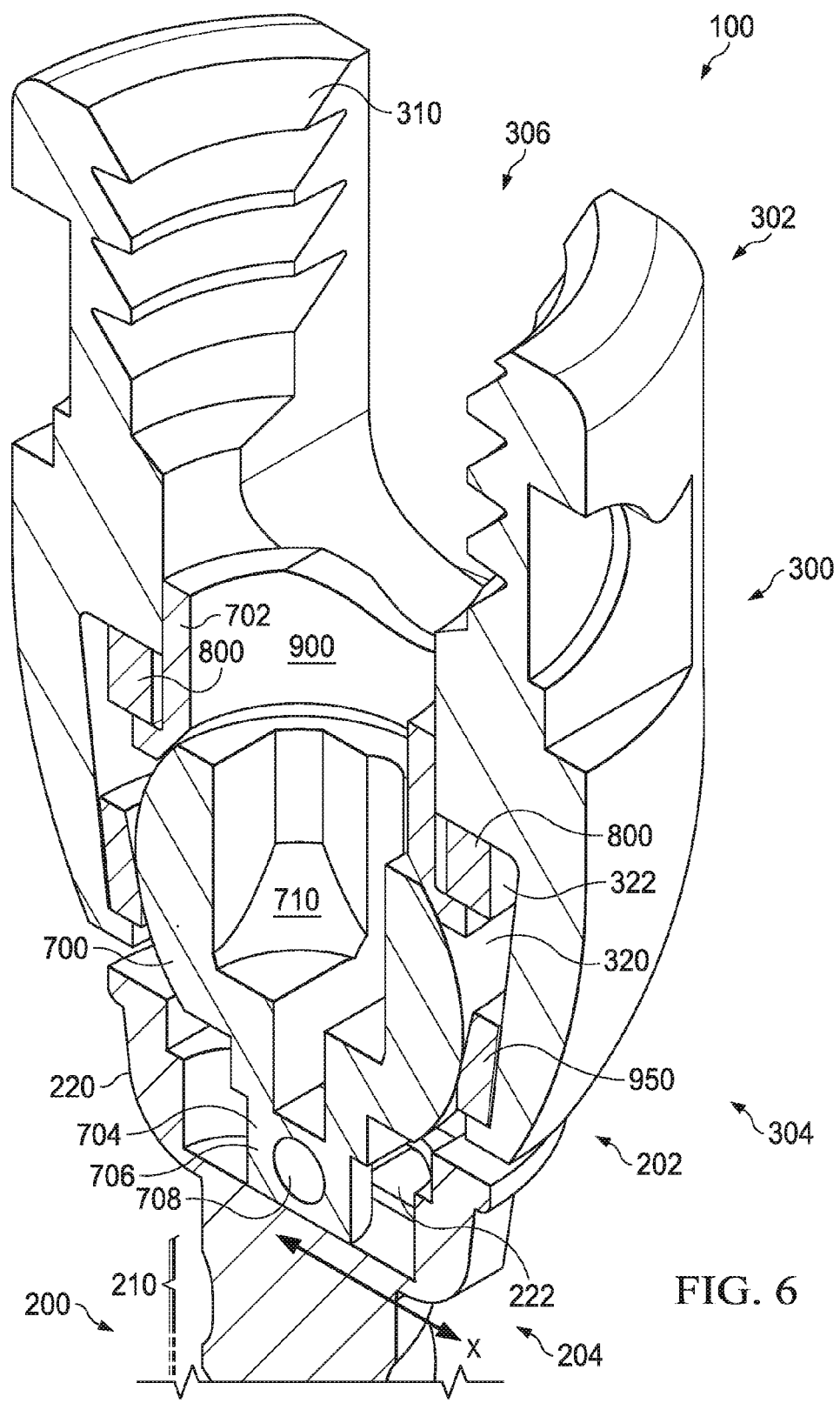
FIG. 6 illustrates a close-up, cross-sectional perspective view of a translational pedicle screw system according to one embodiment of the present disclosure.

Another embodiment of the present disclosure is shown in FIG. 6. FIG. 6 illustrates a close-up, cross-sectional perspective view of a translational pedicle screw system 100 according to one embodiment of the present disclosure. As shown, the bone screw system 100 may also comprise the bone screw 200 and the saddle 300. The bone screw system 100 may further comprise a removable bone screw head 700.

In the embodiment of FIG. 6, the bone screw 200 may comprise the distal end 204 with a shank portion 210. The shank portion 210 may comprise a threading thereon, wherein the threading may be operable to be secured or fastened into a bone such as a pedicle portion of a spine. The proximal end 202 of the bone screw 200 may comprise an attachment section 220.

The attachment section 220 may be configured to removably engage with the removable bone screw head 700. In some embodiments, the attachment section 220 may comprise a lateral recess 222. The lateral recess 222 may be an inner cavity extending laterally outwards to create two lateral slots or recesses along opposing sides of the proximal end 202 of the bone screw 200. The removable bone screw head 700 may comprise a substantially spherical geometry at a proximal end 702 and an elongated engagement section 706 at a distal end 704. The engagement section may comprise a lateral pin 708 disposed in an orientation substantially orthogonal to the longitudinal axis of the bone screw 200. Removably engaging the attachment section 220 with the removable bone screw head 700 may comprise securing the lateral pin 708 of the removable bone screw head 700 in the lateral recess 222 of the attachment section 220. For example, removably engaging the attachment section 220 may comprise positioning a lateral pin 708 in a diagonal orientation within the lateral recess 222. A diagonal orientation may be advantageous as the lateral pin 708 may have a dimension equal to or greater than the width of the lateral recess 222. Thus, positioning the lateral pin 708 along the diagonal may allow for more room to accommodate said component. Once diagonally disposed, the removable bone screw head 700 may then be rotated or turned such that the lateral pin 708 may be received into and may be locked within the outward slots or openings of the lateral recess 222. A turn or rotation of the removable bone screw head 700 relative to the lateral recess 222 may advantageously secure the removable bone screw head 700 therein. The removable bone screw head 700 may then be limited to a translational motion along an axis of the lateral recess 222. In FIG. 6, the axis of translational motion is indicated as axis X. Described further, the removable bone screw head 700 may be disposed in and may rest within the lateral recess 222. The removable bone screw 700 may then translate along the X axis of the attachment section 220 as defined by the lateral recess 222. One of ordinary skill in the art would appreciate other methods and/or variations of securing the removable bone screw head 700 to the attachment section 220 without departing form the present disclosure. Such methods may provide for the translational motion along axis X.

Figures 7A, 7B:
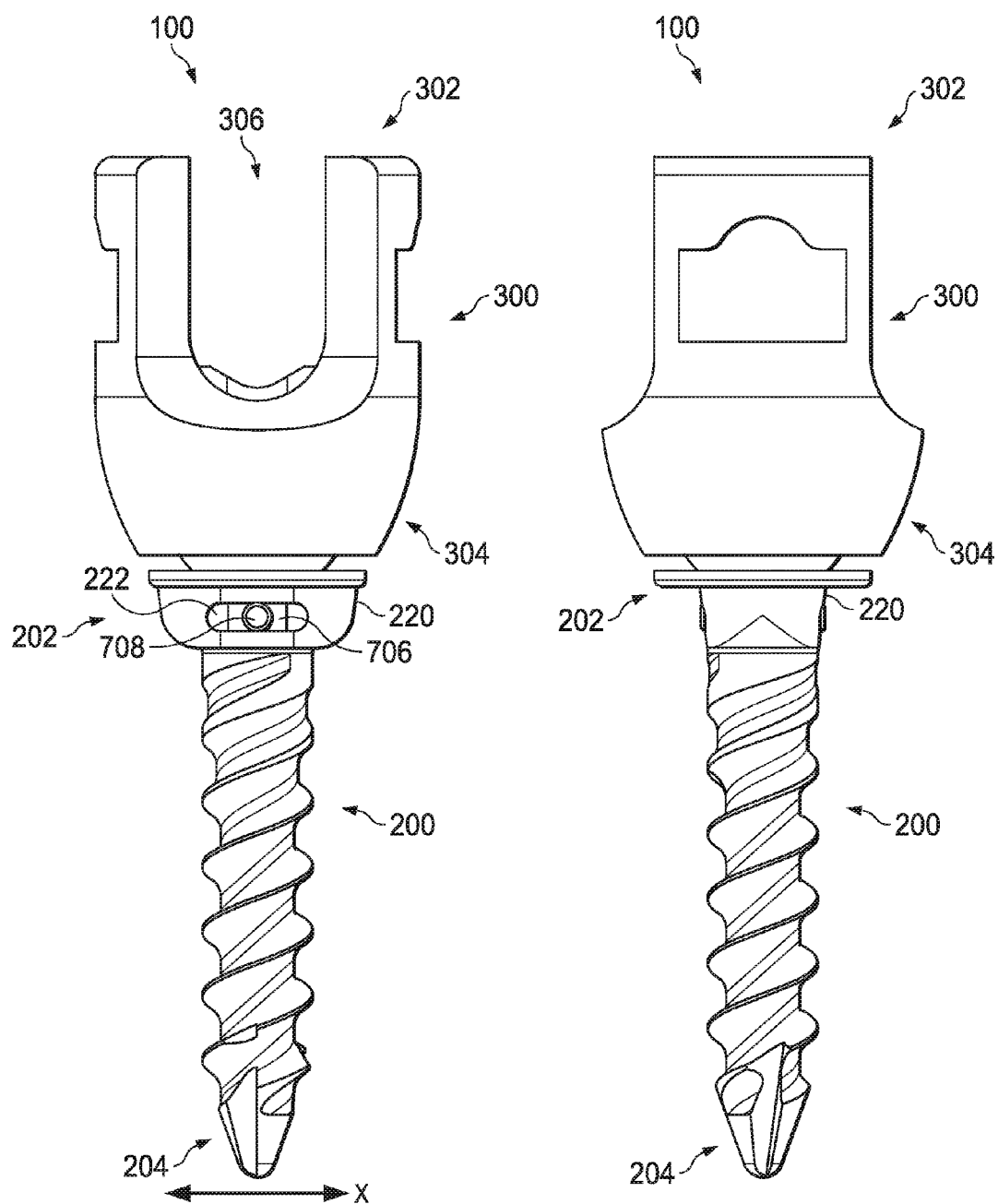
FIG. 7A illustrates a profile view of a translational pedicle screw system according to the embodiment shown in FIG. 6.
FIG. 7B illustrates another profile view of a translational pedicle screw system according to the embodiment shown in FIG. 6 and FIG. 7A.

Embodiments of the present disclosure may advantageously provide for a translational movement of the removable bone screw head 700 within the lateral recess 222. FIG. 7A illustrates a profile view of a translational pedicle screw system 100 according to the embodiment shown in FIG. 6. FIG. 7B illustrates another profile view of a translational pedicle screw system 100 according to the embodiment shown in FIG. 6 and FIG. 7A. More specifically, FIG. 7B illustrates the bone screw system 100 of FIG. 7A rotated 90 degrees about a longitudinal axis. As shown in FIG. 7A and FIG. 7B, the saddle 300 may be positioned relative to the bone screw 200 such that the longitudinal axis of the saddle 300 passing from the proximal end 302 to the distal end 304 may be aligned with the longitudinal axis of the bone screw 200 passing from the proximal end 202 to the distal end 204. Such position may be similar to that of a traditional bone screw system wherein a saddle rests directly atop a bone screw 300. Embodiments of the present disclosure may advantageously allow for translational movement of the saddle 300 relative to the bones screw 200. Such movement may be facilitated by the translational movement of the lateral pin 708 within the lateral recess 222.

Figure 7C:
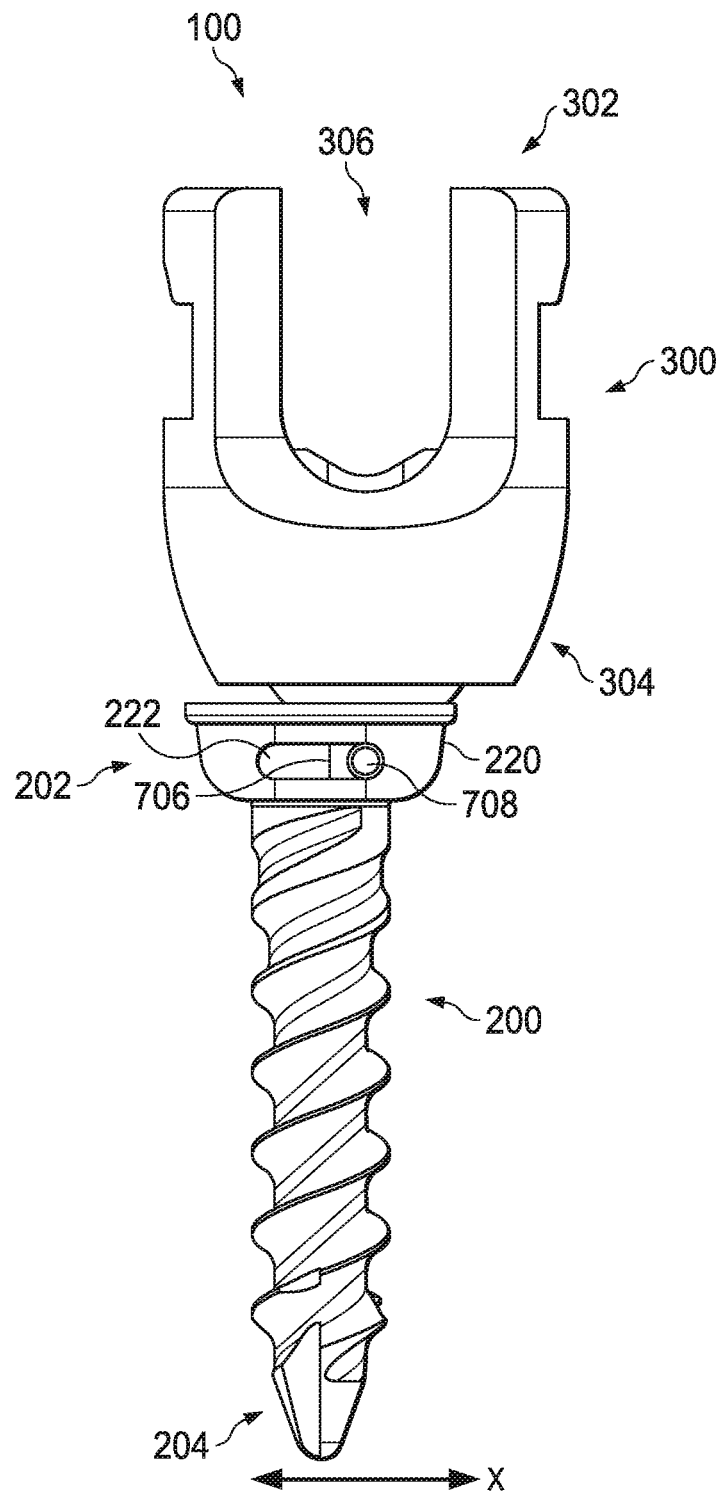
FIG. 7C illustrates another profile view of a translational pedicle screw system according to the embodiment shown in FIG. 6, FIG. 7A, and FIG. 7B.

FIG. 7C illustrates another profile view of a translational pedicle screw system 100 according to the embodiment shown in FIG. 6 and FIG. 7A. More specifically, FIG. 7C illustrates a profile view in the same perspective as shown in FIG. 7A. However, in FIG. 7C, the saddle 300 is translationally displaced relative to its position in FIG. 7A. A translation axis of the saddle 300 is indicated as axis X in FIG. 7A and FIG. 7C. As shown, the lateral pin 708 may be operable to translate or move within the lateral recess 222 of the attachment section 220 of the bone screw 200. Since the lateral pin 708 may be attached, secured to, or machined as part of the removable bone head screw 700, movement of the lateral pin 708 may result in a movement of the removable bone head screw 700. Further, a movement of the removable bone head screw 700 may result in a movement of the saddle 300 secured thereon. As shown in FIG. 7C, the saddle 300 is in a different position than in FIG. 7A. More specifically, the saddle 300 may be positioned relative to the bone screw 200 such that the longitudinal axis of the saddle 300 passing from the proximal end 302 to the distal end 304 is not aligned with, and is further to the right of the longitudinal axis of the bone screw 200 passing from the proximal end 202 to the distal end 204.

In some embodiments, the range of translational movement of the lateral pin 708 within the lateral recess 222 may be about 3 mm to about 6 mm. The range of translational movement may be varied without departing from the present disclosure. In some embodiments, a larger lateral recess 222 may advantageously provide for a greater translational freedom of the removable bone head screw 700, and the saddle 300 secured thereon. Such greater translational freedom may allow the saddle 300 to be more easily positioned for alignment with a mounting rod. However, a greater lateral recess 222 may require larger components or attachment sections 220 with larger dimensions. Thus, greater incisions may need to be made during surgery to accommodate the larger dimensions. In some embodiments, providing for a smaller lateral recess 222 with reduced translational movement along axis X may advantageously allow for smaller components to be used. Thus, smaller incisions may be made during surgery to allow for a less invasive procedure.

The removable bone screw head 700 may comprise a recess 710 thereon. The recess 710 may be disposed at the top or proximal end 702 of the removable bone screw head 700. The recess 710 may comprise a geometric indentation such as a hex, star, hexagon, rectangular, or heptagon operable to engage with a corresponding geometric protrusion. The recess 710 may be operable to engage with a fastening mechanism such as a screw driver or a counter torque wrench. Such engagement may allow the removable bone screw head 700, secured to the bone screw 200, to be fastened into a pedicle portion of a spine or other bone region.

The saddle 300 of the embodiments shown in FIG. 7A, FIG. 7B, and FIG. 7C, may comprise the mounting rod receiving channel 306 disposed at the proximal end 302 of the saddle 300. The mounting rod receiving channel 306 may be configured to receive a mounting rod therein. A mounting rod may serve to provide stability between or among a plurality of saddles 300 in the bone screw system 100. The mounting rod receiving channel 306 may comprise an internal threading 310 operable for receiving a compression element, such as a set screw, therein.

The saddle 300 may further comprise a distal recess 320 disposed at the distal end 304 of the saddle 300. The distal recess 320 may comprise a cavity or opening operable to receive the removable bone screw head 700. The distal recess 320 may be sized to securely receive and fit the removable bone screw head 700 therein. In some embodiments, compressing opposing sides of the proximal end 302 of the saddle 300 may be operable to expand the distal end 304 and the distal recess 320 of the saddle 300. Such expansion may allow a removable bone screw head 700 to be readily received into the distal recess 320. Furthermore, such expansion may advantageously promote a modular nature of the components of the bone screw system 100 and allow the saddle 300 to be easily "snapped on" to a removable bone screw head 700. Thus, even after a bone screw 200 may have been fastened into a bone, the saddle 300 may be removed, replaced, or readjusted as needed. Such modular design may be helpful when choosing among differently sized saddles 300 or saddles 300 with other distinguishing features.

In some embodiments of the present disclosure, the distal recess 320 may further comprise a proximal undercut 322 or an undercut disposed along the proximal end of the distal recess 320. The undercut 322 may be configured to receive at least one biasing component 800 therein. Referring to FIG. 6, the embodiment shown comprises two biasing components 800, wherein each of the two biasing components 800 are disposed on opposing sides of the removable bone screw head 700. The biasing components 800 may be operable to bias against the saddle 300 and the removable bone screw head 700. The bias or expansive forces exhibited by the biasing components 800 may advantageously increase frictional forces within the saddle 300 and the bone screw system 100. Thus, a more secure or stable bone screw system 100 may be provided.

Figure 8:
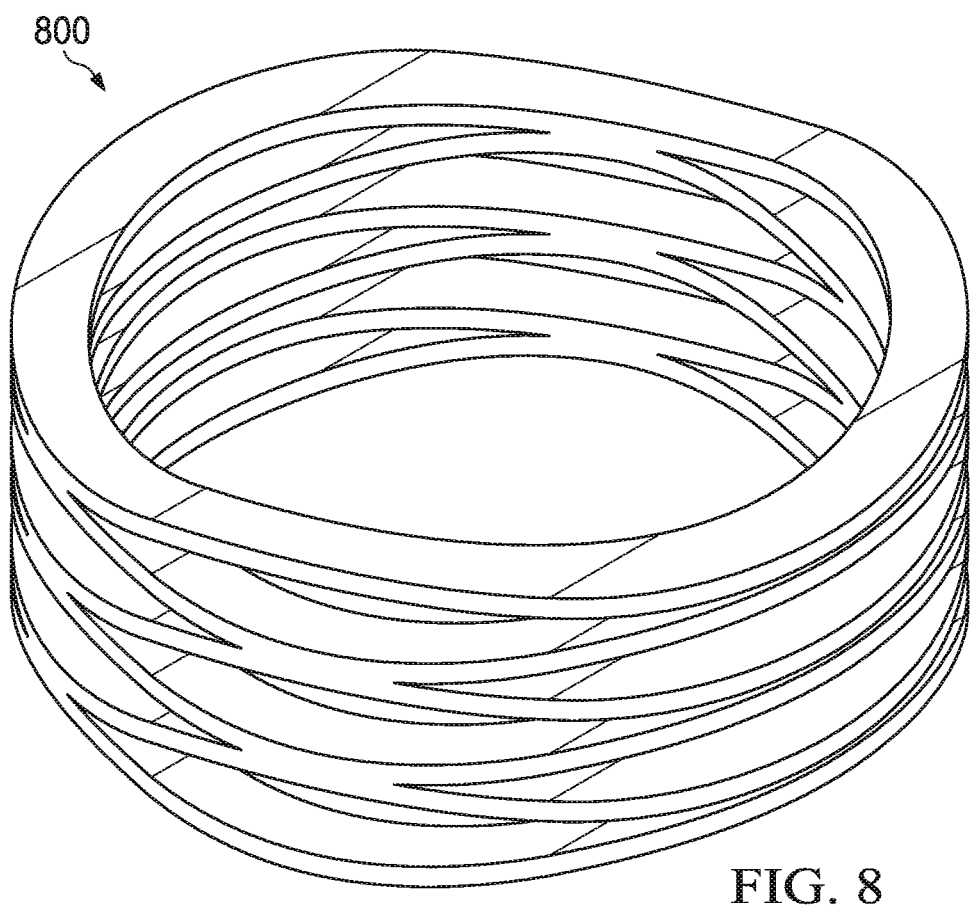
FIG. 8 illustrates a perspective view of a wave spring of a translational pedicle screw system according to one embodiment of the present disclosure.

In some embodiments, the biasing components 800 may be wave springs 800. Referring to FIG. 8, a perspective view of the wave spring 800 according to one embodiment of the present disclosure is shown. As shown in FIG. 8, the wave spring 800 may comprise a series of coils or wave-like structures. Wave springs 800 may advantageously serve as load bearing devices in small spaces. An intertwining or layered structure may allow wave springs 800 to produce substantial expansive forces while maintaining a small size. Various wave springs 800 may be used with the embodiments of the present disclosure. Such wave springs 800 may include, for example, crest-to-crest wave springs, single turn wave springs, linear springs, nested wave springs, and interlaced wave springs. Furthermore, the turns and waves of the wave springs may be easily adjusted to accommodate or provide for stronger force or meet requirements or design needs of the bone screw system 100. Additionally, biasing components 800 other than wave springs may also be used to provide forces against saddle 300 and bone screw 200 without departing from the present disclosure.

Referring to FIG. 6, the bone screw system 100 may comprise a pressure cap 900. The pressure cap may be operable to be disposed distal to the proximal end 302 of the saddle 200 and to bias against components distal in the saddle 300, such as the removable bone screw head 700. In some embodiments, the pressure cap 900 may comprise an annular protrusion at a distal end. Such annular protrusion may be configured to provide or define a receiving space in the undercut 322 of the saddle 300. The receiving space may allow the biasing components 800 to be received therein. In some embodiments, the pressure cap 900 may be monolithic with the saddle 300. Described different, the pressure cap 900 may be machined together with the saddle 300

In some embodiments, a retaining ring 950 may be disposed within the distal channel 320. The retaining ring 950 may advantageously secure the removable bone screw head 700 in the distal channel and provide for a more stable system.

In any of the embodiments of the present disclosure, the materials may be chosen and may be varied to fit a number of functional and design considerations. For example, the bone screw 200, the removable bone screw head 700, and the saddle 300 may comprise materials such as titanium, titanium alloys (ex. Ti-6Al-4V), aluminum, stainless steel, or cobalt chrome alloy, polymer (ex. Radel, Ultem, or PEEK) or carbon filled polymer. Components such as the retaining ring 950 may comprise similar materials or may comprise materials such as nitinol. Variations may be made to the composition of aforementioned components without departing from the present disclosure.

Referring to FIG. 6, the bone screw system 100 may comprise a saddle 300 with a height of about 2 mm to about 6 mm. The removable bone screw head 700 may comprise a diameter of about 7 mm to about 11 mm. The lateral pin 708 may comprise a diameter of about 2.5 mm to about 5 mm. The lateral recess 222 may comprise an outward or lateral slot of about 3 mm to about 10 mm. Dimensions of the various components of the present disclosure may be varied as needed or desired to achieve a number of functional or design goals. Such variations in dimensions may provide for translational pedicle screw systems 100 without departing from the present disclosure.

According to another aspect of the present disclosure, methods of assembling the translational pedicle screw system 100 are provided. Methods may comprise providing the bone screw 200 and removably engaging the attachment section 220 with the removable bone screw head 700. Methods may further comprise securing the saddle 300 over the removable bone screw head 700. For example, the removable bone screw head 700 may be received within the distal recess 320 of the saddle 300. In some embodiments, methods of assembly may comprise compressing opposing sides of the proximal end 302 of the saddle 300 such that the distal end 304 and the distal recess 320 may be expanded to receive the removable bone screw head 700.

Methods of assembly may further comprise disposing the retaining ring 950, biasing members 800, and/or the pressure cap 900 within the saddle 300. Such steps may be performed prior to securing the saddle 300 onto the removable bone screw head 700. Securing the saddle 300 onto the removable bone screw head 700 may be performed either before or after the bone screw 200 has been fastened or otherwise secured into a bone region such as a pedicle region of the spine.

Methods of assembling the pedicle screw system 100 may also comprise translating or moving the saddle 300 relative to the bone screw 200 such that the saddle 300 is in a more appropriate or more desired position to receive a mounting rod therein.

Additional Description

The above embodiments are provided by way of example only. Features and aspects of the various embodiments may be adjusted or combined without departing from the present disclosure. For example, an embodiment of a bone screw system 100 making use of a discoidal section 214 of a bone screw 200 may also comprise a distal channel 308 of a saddle 300 to allow the discoidal section 214 to translate therein. Furthermore, aspects or features of components described in one embodiment may apply or may be present in other embodiments of bone screw systems as well. Such adjustments or combinations of features would be apparent to one of ordinary skill in the art having the benefit of the present disclosure.

As will be understood by those skilled in the art who have the benefit of the instant disclosure, other equivalent or alternative compositions, devices, methods, and systems for translational bone screw systems can be envisioned without departing from the description contained herein. Accordingly, the manner of carrying out the disclosure as shown and described is to be construed as illustrative only.

One of ordinary skill in the art may make various changes in the shape, size, number, and/or arrangement of parts without departing from the scope of the instant disclosure. For example, the position and number of pressure caps, retention rings, and/or holding pins may be varied. In some embodiments, saddles may be interchangeable. Interchageability may allow saddles to be custom adjusted (e.g., by size). In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/− about 50%, depicted value +/− about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for translational bone screw systems may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

The invention claimed is:

1. A spinal fixation system comprising:
    a bone screw comprising:
        a bone screw head at a proximal end; and
        a shank portion at a distal end;
    a saddle comprising:
        a mounting rod receiving channel disposed at a proximal end of the saddle; and
        a distal channel disposed at a distal end of the saddle, wherein the distal channel receives a retaining ring and the bone screw head therein;
    a pressure cap disposed within the saddle between a mounting rod and the bone screw, the pressure cap comprising:
        a proximal portion disposed within an undercut of the saddle; and
        a distal portion comprising an annular extension; and
    wherein the retaining ring disposed within the distal channel of the saddle, the retaining ring having an outer circumference adjacent to an inner wall of the distal channel of the saddle;
    wherein the distal channel of the saddle further comprises:
        a longer length in a first direction, the longer length being configured to provide translational motion of the bone screw head along a translational axis within the distal channel of the saddle; and a shorter length in a second direction, the shorter length being configured to restrict motion of the bone screw head along an axis within the distal channel of the saddle;

wherein the axis is orthogonal to the translational axis and to a longitudinal axis of the distal channel.

2. The spinal fixation system of claim 1, wherein the bone screw head comprises a recess thereon, and wherein the recess is operable to engage with a fastening mechanism.

3. The spinal fixation system of claim 1, wherein the shank portion comprises threading thereon configured to be secured into a pedicle portion of a bone.

4. The spinal fixation system of claim 1, wherein the mounting rod receiving channel is configured to receive a mounting rod therein.

5. The spinal fixation system of claim 1, wherein a proximal end of the mounting rod receiving channel comprises an internal thread for receiving a compression element therein.

6. The spinal fixation system of claim 1, wherein the annular extension of the pressure cap is configured to bias against the bone screw head of the bone screw.

7. The spinal fixation system of claim 1, wherein the saddle further comprises at least one saddle pin hole disposed on a wall of the saddle.

8. The spinal fixation system of claim 7, wherein the pressure cap further comprises at least one pressure cap pin hole disposed on a wall of the pressure cap; wherein the at least one saddle pin hole is configured to align with the at least one pressure cap pin hole; and wherein a holding pin may be received through the aligned saddle pin hole and pressure cap pin hole.

9. The spinal fixation system of claim 1, wherein the bone screw has about 5 mm of translational motion about the translational axis.

10. The spinal fixation system of claim 1, wherein the pressure cap comprises nitinol.

11. The spinal fixation system of claim 1, wherein the retaining ring comprises nitinol.

12. The spinal fixation system of claim 1, wherein the saddle has a length of about 5 mm to about 12 mm.

13. The spinal fixation system of claim 1, wherein the saddle has a width of about 5 mm to about 8 mm.

14. A method of assembling a spinal fixation system, the method comprising:
providing a saddle, the saddle comprising:
a mounting rod receiving channel disposed at a proximal end of the saddle; and
a distal channel disposed at a distal end of the saddle;
disposing a pressure cap within the saddle, the pressure cap comprising:
a proximal portion disposed within an undercut of the saddle; and
a distal portion comprising an annular extension having a distally oriented protruding edge;
disposing a retaining ring within the distal channel of the saddle such that an outer circumference of the retaining ring is adjacent to an inner wall of the distal channel of the saddle; and
receiving in the distal channel a bone screw head of a bone screw, the bone screw comprising:
the bone screw head at a proximal end; and
a shank portion at a distal end,
wherein the distal channel of the saddle provides translational motion of the bone screw along a translational axis within the saddle, and restricts motion of the bone screw head along an axis within the distal channel of the saddle;
wherein the axis is orthogonal to the translational axis and to a longitudinal axis of the distal channel, and
wherein the protruding edge exerts a compressive force on a top surface of the retaining ring when the bone screw system is assembled.

\* \* \* \* \*